(12) United States Patent
Ishida et al.

(10) Patent No.: US 6,660,380 B1
(45) Date of Patent: Dec. 9, 2003

(54) ZINC OXIDE PARTICLES HAVING SUPPRESSED SURFACE ACTIVITY AND PRODUCTION AND USE THEREOF

(75) Inventors: Kuniteru Ishida, Fukushima (JP); Hiroshi Hakozaki, Fukushima (JP); Keita Kobayashi, Fukushima (JP); Keiji Ono, Fukushima (JP)

(73) Assignee: Sakai Chemical Industry Co., Ltd., Osaka (JP)

( * ) Notice: Subject to any disclaimer, the term of this patent is extended or adjusted under 35 U.S.C. 154(b) by 0 days.

(21) Appl. No.: 09/743,580

(22) PCT Filed: May 11, 2000

(86) PCT No.: PCT/JP00/03046

§ 371 (c)(1), (2), (4) Date: Jul. 2, 2001

(87) PCT Pub. No.: WO00/69776

PCT Pub. Date: Nov. 23, 2000

(30) Foreign Application Priority Data

| May 12, 1999 | (JP) | 11-132029 |
| Jun. 16, 1999 | (JP) | 11-208070 |
| Jun. 18, 1999 | (JP) | 11-209661 |

(51) Int. Cl.[7] .................................................. B32B 5/16
(52) U.S. Cl. ...................... 428/403; 427/215; 427/219; 427/397.7; 428/405
(58) Field of Search ................................. 428/403, 405; 427/215, 219, 397.7

(56) References Cited

U.S. PATENT DOCUMENTS

| | | | | |
|---|---|---|---|---|
| 3,853,574 A | * | 12/1974 | Ferrigno | 106/288 B |
| 4,801,445 A | * | 1/1989 | Fukui et al. | 424/69 |
| 5,093,099 A | * | 3/1992 | Haishi et al. | 423/622 |
| 5,188,763 A | * | 2/1993 | Chenot et al. | 252/301.5 |
| 5,424,055 A | * | 6/1995 | Hayashi et al. | 423/622 |
| 5,536,492 A | * | 7/1996 | Mitchnick et al. | 424/59 |
| 5,670,139 A | * | 9/1997 | Allard et al. | 424/59 |
| 5,672,427 A | * | 9/1997 | Hagiwara et al. | 428/403 |
| 6,086,666 A | * | 7/2000 | Noguchi et al. | 106/425 |

FOREIGN PATENT DOCUMENTS

| JP | 8-059890 | 3/1998 |
| JP | 10-120418 | 5/1998 |
| JP | 11-256133 | 9/1999 |
| JP | 11-279358 | 10/1999 |

* cited by examiner

Primary Examiner—H. Thi Le
(74) Attorney, Agent, or Firm—Wenderoth, Lind & Ponack, LLP

(57) ABSTRACT

The invention provides a zinc oxide particle having suppressed surface activity which gives safe and effective UV ray shielding ability (especially at longer wavelengths) to a variety of products such as resin molds, coating compositions or cosmetics, and a process for the production of the same.

The zinc oxide particle of the invention has on the surface a cover layer formed of zinc silicate in an amount of 0.5–50% by weight in terms of zinc silicate ($Zn_2SiO_4$) relative to the zinc oxide. The zinc oxide particle which contains solid solution iron or cobalt therein as well as a cover layer formed of zinc silicate has effective UV ray shielding ability at much longer wavelengths while it is suppressed in the surface activity.

14 Claims, 3 Drawing Sheets

ZINC OXIDE PARTICLES HAVING SUPPRESSED SURFACE ACTIVITY AND PRODUCTION AND USE THEREOF

FIELD OF THE INVENTION

This invention relates to zinc oxide particles having a cover layer formed of zinc silicate on the surface and hence having not only greatly suppressed surface activity and high shielding ability of ultraviolet (UV) rays inclusive of those of a long wavelength region around 400 nm but also high transparency to visible light. The invention further relates to a process for production of such zinc oxide particles.

BACKGROUND OF THE INVENTION

In recent years, the increase of UV radiation which reaches to the surface of the earth or the biosphere as a result of the depletion of the ozone layer has come to public notice as a contributing factor to the damage to the human health.

Under these circumstances, the interest in the protection of the human body from UV rays is accordingly increasing. As already known, there are two regions of UV rays reaching the surface of the earth or the biosphere, B-region UV rays (UV-B) at wavelengths of 290–320 nm and A-region UV rays (UV-A) at wavelengths of 320–400 nm. More recently, there is growing a great interest in the protection of the human body from UV-A rays at longer wavelengths as well as UV-B rays.

Organic UV-absorbers have been conventionally used in resin films, coating compositions (i.e., paints) or sunscreen cosmetics. However, the organic UV-absorber has a problem of bleeding. That is, it migrates to the surface layer from the inside of resin molds such as resin films or coatings as time passes. The organic UV-absorber has a further problem that its UV shielding effect diminishes as time passes owing to the photodecomposition.

Furthermore, the conventional organic UV-absorbers are stimulative to the human skin when they are used in cosmetics, and in addition, they have a limited spectrum of UV rays which they can absorb. Thus, there is now a great demand for a material which is able to shield a broader UV spectrum.

On the other hand, inorganic UV-absorbers have been also heretofore widely used, especially ultrafine particles of rutile titanium dioxide, in the field of coating compositions or cosmetics. However, rutile titanium dioxide has a large refractive index (2.7) so that it has a fair hiding power in spite of the fact that they are adjusted to be ultrafine in their particle size.

Accordingly, when rutile titanium dioxide is incorporated in resin molds or coating compositions, it is poor in transparency to visible light. Further, when a sunscreen agent which contains rutile titanium dioxide therein is applied to the human skin, the titanium dioxide scatters blue light strongly so that the skin often looks pale and unhealthy. As a further problem, the rutile titanium dioxide is not enough in shielding effect of UV-A rays.

To cope with these problems, a composite oxide composed of Ti, Si and Fe was proposed that is excellent in shielding ability of UV-A rays (JP-A-9-30933). Iron-containing rutile titanium dioxide ultrafine particles were also proposed as a useful material for sun blocking cosmetics which look less pale when being applied to the human skin (JP-A-5-330825). However, these modified titanium dioxides are still insufficient in shielding ability of UV-A rays. Further, these modified titanium dioxides have still a large refractive index so that they have a tendency to hide the human skin when they are applied to the human skin. Accordingly, if they are incorporated in sunscreen cosmetics in such an amount that they can shield effectively UV-A rays, they have no transparent appearance when being applied to the human skin.

Ultrafine particles of zinc oxide have an absorption edge at a wavelength of 380 nm, and they are able to shield most part of UV-A rays as well as UV-B rays, and moreover, they have a small refractive index (2.0) and highly transparent. Because the ultrafine particles of zinc oxide are as such, they attract a great deal of attention as a UV-absorber in recent years. Thus, they have been heretofore used mainly in the field of cosmetics, but they are now spreading their application in various fields on account of their excellent properties in addition to cosmetics.

However, on the other hand, various problems have been indicated when the known ultrafine zinc oxide particles are used as UV-absorbers. For example, when they are used in thermoplastic resins such as polyethylene terephthalate or polycarbonate, they promote the decomposition of these resin, and deteriorate their moldability remarkably. When the known ultrafine zinc oxide particles are used in coating compositions, the zinc oxide reacts with a binder resin in the compositions to increase the viscosity of the composition and to gel the composition as time passes.

Furthermore, when the resin molds or coatings which contain the known ultrafine zinc oxide particles therein are exposed outdoors, there is a problem that the zinc oxide decomposes photocatalytically the resins around the zinc oxide particles. With regard to cosmetics containing the known ultrafine zinc oxide particles therein, there is a fear that reactive oxygen species are photocatalytically generated at the surface of the particles.

Zinc oxide has a further property that it is inherently soluble slightly in water and, as is known, the physiological effect of the thus dissolved zinc ion has been utilized as astringent in the field of cosmetics from long ago. The chemical reactivity of zinc oxide to saponify fatty acids to form metal soaps is often utilized to absorb sebum secreted by the human skin to improve makeup wear, or as deodorant to absorb the body odor components.

These physiological activity and the chemical reactivity of zinc oxide become stronger as it is finer in particle size and accordingly, it is demanded to restrain the surface activity of zinc oxide particles, in particular, ultrafine zinc oxide particles, from the viewpoint of its safety for the human skin.

To meet the demand as mentioned above, the present inventors already proposed to treat the surface of zinc oxide particles with high density silica in order to restrain the surface activity which zinc oxide inherently possesses (JP-A-11-336316). However, such a method as surface treating or coating forms a cover layer formed of hydrated oxides such as hydrated silica or alumina on the surface of zinc oxide particles. Accordingly, when zinc oxide particles are treated by such a method and incorporated in high temperature molding resins or high temperature baking coating compositions such as powdery coating compositions or precoat metals, there arises a problem that dull finish of resin molds or coatings results due to the coating layer formed of hydrated oxides on the surface of zinc oxide particles as mentioned above.

The thus hydrated oxide-coated zinc oxide particles have also a fatal defect that they promote the hydrolysis of resins such as polyethylene terephthalate or polycarbonate resin.

In addition, food packaging film must shield UV rays at wavelengths up to of about 400 nm depending upon the kind of foods therein, and an topcoat layer of two-coat automobile coating system composed of top coats and primer coats must prevent the transmission of UV rays at wavelengths of up to about 400 nm or more. However, ultrafine zinc oxide particles alone fail to shield the rays at wavelengths of more than 380 nm.

The invention has been completed in order to solve the problems involved in the zinc oxide particles known heretofore, in particular, the known ultrafine zinc oxide particles.

Accordingly, it is an object of the invention to provide zinc oxide particles, preferably ultrafine zinc oxide particles, which have suppressed surface activity and give safe and effective UV ray shielding ability to a variety of products such as resin molds, coating compositions or cosmetics free from the problems as mentioned hereinabove.

It is a further object of the invention to provide a process for the production of such ultrafine zinc oxide particles having suppressed surface activity.

It is also an object of the invention to provide uses of such ultrafine zinc oxide particles as above mentioned, particularly resin molds, coating compositions or cosmetics.

It is still an object of the invention to provide ultrafine zinc oxide particles which are able to shield UV rays at longer wavelengths of about 400 nm.

DISCLOSURE OF THE INVENTION

The invention provides a particulate zinc oxide or a zinc oxide particle having suppressed surface activity characterized in that it has on the surface a cover layer formed of zinc silicate in an amount of 0.5–50% by weight, preferably 1–15% by weight, in terms of zinc silicate (zinc orthosilicate, $Zn_2SiO_4$) relative to the zinc oxide.

Herein the invention, when the terms "in terms of zinc silicate" are used, the "zinc silicate" means zinc orthosilicate, $Zn_2SiO_4$.

According to the invention, water-insoluble zinc compounds which are converted to zinc oxide by heating in the air can be used as raw materials (i.e., starting materials) for the zinc oxide particles of the invention, as mentioned in detail hereinafter, as well as particles of zinc oxide itself. Water-soluble zinc salts which form the above-mentioned water-insoluble zinc compounds when they are neutralized with a neutralizing agent can be also used as starting materials particularly when particles of zinc oxide which have not only solid solution iron or cobalt atoms therein but also a cover layer formed of zinc silicate on the surface are to be obtained, as mentioned in detail hereinafter. In these cases, when the terms "relative to the zinc oxide" are used, they mean "relative to the zinc oxide" which is formed—in a theoretical amount, strictly speaking—from the above-mentioned water-insoluble zinc compounds or water-soluble zinc salts used as raw materials for zinc oxide in a manner as mentioned above.

The zinc oxide particles which have suppressed surface activity are obtainable by adding aqueous solutions of a water-soluble silicate and a water-soluble zinc salt to an aqueous suspension of particles of water-insoluble zinc compound in such a chemically stoichiometric ratio so that they form zinc silicate ($Zn_2SiO_4$) as well as in an amount of 0.5–50% by weight in terms of zinc silicate ($Zn_2SiO_4$) relative to the zinc oxide, washing with water and drying the resulting product, and calcining the product at a temperature of 300–1200° C. thereby forming zinc oxide particles and a cover layer formed of zinc silicate on the surface of the particles.

There are used as the above-mentioned water-insoluble zinc compound, for example, zinc oxide, zinc hydroxide, zinc carbonate, basic zinc carbonate, zinc sulfide or zinc oxalate.

When zinc oxide particles which contain iron or cobalt atoms therein in the form of solid solution are to be obtained, prior to the addition of aqueous solutions of a water-soluble silicate and a water-soluble zinc salt to an aqueous suspension of particles of water-insoluble zinc compound in such a chemically stoichiometric ratio so that they form zinc silicate ($Zn_2SiO_4$) in the process mentioned above, particles of zinc compound which have hydrated iron oxide or cobalt oxide precipitates on the surface in a predetermined amount relative to the zinc oxide (to be formed) are first prepared. Then, aqueous solutions of a water-soluble silicate and a water-soluble zinc salt are added to an aqueous suspension of particles of water-insoluble zinc compound in such a chemically stoichiometric ratio so that they form zinc silicate ($Zn_2SiO_4$), and the resulting product is washed with water and dried, and then the product is calcined at a temperature of 300–1200° C.

In this way, the zinc compound particles are converted to zinc oxide particles, that is, zinc oxide particles are formed from the zinc compound particles and iron or cobalt atoms are diffused into the thus formed zinc oxide particles to form a solid solution while forming a cover layer of zinc silicate on the surface of the zinc oxide particles.

It is usually necessary to calcine the zinc oxide particles at a temperature at least of several hundred degrees, preferably at a temperature of as high as of 600–1000° C. in order that iron or cobalt atoms form a solid solution in the crystals of zinc oxide particles. However, when zinc oxide particles are heated at such a high temperature, the particles grow excessively to fail to provide zinc oxide particles of high transparence. Nevertheless, according to the invention, zinc oxide particles do not sinter to form large particles if they are heated at such a high temperature because of the cover layer formed of zinc silicate on the surface, and hence ultrafine zinc oxide particles are obtained containing solid solution iron or cobalt therein.

The invention further provides a particulate zinc oxide or zinc oxide particle having suppressed surface activity characterized in that it has a first cover layer on the surface comprising zinc silicate in an amount of 0.5–50% by weight in terms of zinc silicate ($Zn_2SiO_4$) relative to the zinc oxide while the particle may contain iron or cobalt atoms in the form of solid solution, and a second coating layer comprising oxides of at least one element selected from the group consisting of Al, Si, Zr, Sn, Sb and rare earth elements in an amount of 0.5–30% by weight in terms of oxides relative to the zinc oxide on the first cover layer.

The above zinc oxide particle is obtained by preparing zinc oxide particle having a cover layer formed of zinc silicate on the surface while it may contain solid solution iron or cobalt, adding an aqueous solution of water-soluble compound of at least one elements selected from the group consisting of aluminum, silicon, tin, zirconium, antimony and rare earth elements to an aqueous suspension of the zinc oxide particle, adding an acid or an alkali as a neutralization agent to neutralize the water-soluble compound and precipitate on the surface of the zinc oxide particle thereby forming the second coating layer on the zinc oxide particle.

The zinc oxide particle of the invention as mentioned above may be further treated with organosilicon compounds, higher fatty acids, higher fatty acid esters, metal soaps, polyhydric alcohols or alkanolamines, if necessary.

The zinc oxide particle of the invention have an average particle size preferably of not more than 0.15 μm.

DESCRIPTION OF PREFERRED EMBODIMENTS

Figure 1:
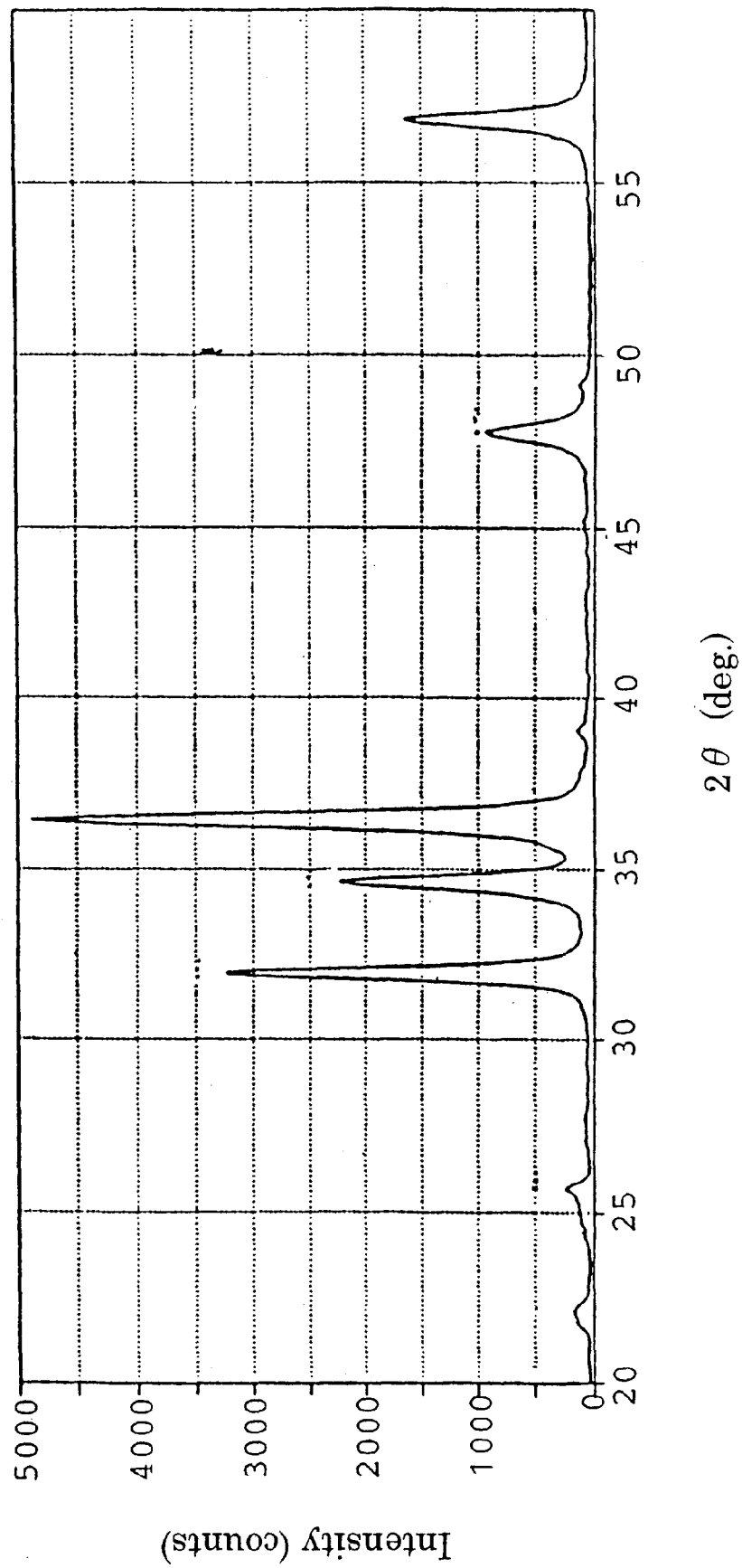
FIG. 1 is an X-ray diffraction chart of zinc oxide particles of the invention (Example 1)

Zinc oxide particles to be used as raw materials in the invention may be produced by oxidation of electrolytic zinc metal, or may be produced by preparing zinc hydroxide by neutralizing an aqueous solution of water-soluble zinc compound such as zinc sulfate or zinc chloride and then heating the thus prepared zinc hydroxide. Other zinc compounds such as zinc carbonate, basic zinc carbonate, zinc sulfide or zinc oxalate also give zinc oxide particles when being heated. However, the process for the production of zinc oxide particles to be used as raw materials are not specifically limited and they may be produced in any manner other than the above.

It is preferred that zinc oxide particles to be used as raw materials in the invention are highly transparent, and accordingly it is preferred that they have an average primary particle size of not more than 0.15 μm. When the zinc oxide particles have an average primary particle size of more than 0.15 μm, they have high hiding power so that when they are used in, for example, resin films, coating compositions or cosmetics, they have inferior transparency and they look whitish. However, zinc oxide particles having an average primary particle size of more than 0.15 μm may be used as raw materials, if necessary. The lower limit of average primary particle size of zinc oxide particles to be used as raw materials is not specifically limited, but it is usually 0.01 μm. Herein the invention, the average primary particle size is defined by arithmetic mean of fixed direction diameters (so called Feret size) in a field of view through a 100000 magnification transmission electron microscope.

The zinc oxide particle of the invention having suppressed surface activity has a cover layer on the surface comprising zinc silicate in an amount of 0.5–50% by weight, preferably 1–15% by weight, in terms of zinc silicate ($Zn_2SiO_4$) relative to the zinc oxide. When the amount of zinc silicate is less than 0.5% by weight relative to the zinc oxide, the surface activity which zinc oxide inherently possesses is hardly suppressed, whereas the amount of zinc silicate is more than 50% by weight relative to the zinc oxide, the UV ray shielding effect which zinc oxide inherently possesses is remarkably reduced.

The zinc oxide particle of the invention which has suppressed surface activity is produced by adding aqueous solutions of a water-soluble silicate and a water-soluble zinc salt to an aqueous suspension of starting zinc oxide particles in such a chemically stoichiometric ratio so that they form zinc silicate ($Zn_2SiO_4$) as well as in an amount of 0.5–050% by weight in terms of zinc silicate ($Zn_2SiO_4$) relative to the zinc oxide, washing with water and drying the resulting product, and then calcining the product at a temperature of 300–1200° C. thereby forming zinc oxide particles and a cover layer formed of zinc silicate on the surface of the particles.

In more detail, it is preferred that the aqueous suspension of starting zinc oxide particles is prepared by grinding zinc oxide particles with, such as a sand mill, and then dispersing the particles in water and that the concentration of starting zinc oxide particles is in the range of 50–250 g/L. However, the method for the preparation of the aqueous suspension of starting zinc oxide particles or the concentration of starting zinc oxide particles is not specifically limited to those above as exemplified.

The aqueous solutions of a water-soluble silicate and a water-soluble zinc salt are then added to an aqueous suspension of starting zinc oxide particles in such a chemically stoichiometric ratio so that they form zinc silicate ($Zn_2SiO_4$) as well as in an amount of 0.5–50% by weight in terms of zinc silicate ($Zn_2SiO_4$) relative to the zinc oxide. If necessary, a neutralization agent is added to the suspension to arrange the pH of the suspension.

Alkali metal silicates such as sodium silicate or potassium silicate are preferably used as the water-soluble silicate mentioned above, while inorganic acid salts such as zinc sulfate or zinc chloride are preferably used as the water-soluble zinc salts, although being not specifically limited to those exemplified. Either of the water-soluble silicate and water-soluble zinc salt may be first added to the aqueous suspension of starting zinc oxide particles, or both may be added at the same time.

The thus treated zinc oxide particles are then separated from the suspension, washed, and dried if necessary, and then the zinc oxide particles are calcined at a temperature in the range of 300–1200° C. in an oxidative atmosphere, for example, in the air. The calcined product is then dry-ground with a suitable means such as a hammer mill, an edge-runner mill or a jet mill to provide zinc oxide in the form of particles of the invention which has a cover-layer formed of zinc silicate on the surface and an average particle diameter in the range of 0.01–0.15 μm.

When the calcining temperature is lower than 300° C., hydrated zinc silicate remains undesirably on the surface of zinc oxide particles, whereas when the calcining temperature is higher than 1200° C., the zinc oxide particles grow excessively to form large particles which are poor in transparency. Accordingly, the calcining temperature is preferably in the range of 500–1100° C. and more preferably in the range of 600–1000° C.

In addition, a cover layer formed of zinc silicate can also be formed by adding a water-soluble silicate to an aqueous suspension of particles of water-insoluble zinc compound, adding a neutralization agent, ageing the resulting mixture, washing the resulting product with water, drying and then calcining the product.

As described above, the zinc oxide particle of the invention has a cover layer formed of zinc silicate on the surface. Thus, when it is dispersed in a medium, the surface of the particle is completely masked or separated from the medium by the cover layer so that the solubility in water or chemical reactivity to fatty acids which zinc oxide inherently possesses is markedly reduced. Furthermore, the zinc oxide particle of the invention is almost completely suppressed in photocatalytic activity which zinc oxide inherently possesses.

According to the invention, a water-insoluble zinc compound which can be converted to zinc oxide by heating in the air, such as zinc hydroxide, zinc carbonate, basic zinc carbonate, zinc sulfide or zinc oxalate, may be used as a starting raw material for the zinc oxide particle of the invention in place of zinc oxide particles. More specifically, aqueous solutions of a water-soluble silicate and a water-soluble zinc salt are added to an aqueous suspension of such particles of water-insoluble zinc compound in such a chemically stoichiometric ratio so that they form zinc silicate ($Zn_2SiO_4$) as well as in an amount of 0.5–50% by weight in terms of zinc silicate ($Zn_2SiO_4$) relative to the zinc oxide, washing with water and drying the resulting product, and then calcining the product at a temperature of 300–1200° C. thereby forming zinc oxide particles and a cover layer formed of zinc silicate on the surface of the particles.

The invention further provides a particulate zinc oxide or a zinc oxide particle which has not only a cover layer formed of zinc silicate on the surface in an amount of 0.5–50% by weight, preferably in an amount of 1–15% by weight, in terms of zinc silicate ($Zn_2SiO_4$) relative to the zinc oxide but also iron in the form of solid solution in an amount of 0.1–20% by weight in terms of iron.

The solid solution iron is contained in the above-mentioned zinc oxide particle in an amount of 0.1–20% by weight, preferably in an amount of 0.5–15% by weight, more preferably in an amount of 1–10% by weight, in terms of iron relative to the zinc oxide. The incorporation of solid solution iron in this way makes it possible to provide ultrafine zinc oxide particles which can shield effectively UV rays at a wavelength region as long as about 400 nm. Such ultrafine zinc oxide particles, when being incorporated in cosmetics, have no undesirable reaction with the other components in the cosmetics, and have no fear of generating reactive oxygen species. Moreover, they can provide cosmetics which appear non-whitish and bare skin-feel finish when being applied to the human skin.

When the amount of the solid solution iron in the zinc oxide particle is less than 0.1% by weight, the zinc oxide is poor in shielding UV-A rays at wavelengths longer than 380 nm, whereas when the amount of the solid solution iron in the zinc oxide particle is more than 20% by weight, a part of iron remains as it is and does not form solid solution together with zinc oxide lattice, and is present separately from zinc oxide particles. Accordingly, when such zinc oxide particles are used in coatings or milky lotions, there arises a problem such as flooding or color separation.

The zinc oxide particle which contains solid solution iron is obtained by adding an aqueous solution of a water-soluble iron salt to an aqueous suspension of zinc oxide particles in an amount of 0.1–20% by weight in terms of iron relative to the zinc oxide, adding a neutralization agent. to the mixture thereby to form a layer of hydrated iron oxide on the surface of the zinc oxide particles, and then, as mentioned hereinbefore, adding aqueous solutions of a water-soluble silicate and a water-soluble zinc salt to the thus prepared aqueous suspension of zinc oxide particles in such a chemically stoichiometric ratio so that they form zinc silicate ($Zn_2SiO_4$) as well as in an amount of 0.5–50% by weight in terms of zinc silicate ($Zn_2SiO_4$) relative to the zinc oxide, washing with water and drying the resulting product, and then calcining the product at a temperature of 300–1200° C. thereby forming zinc oxide particles and a cover layer formed of zinc silicate on the surface of the particles.

In order to precipitate hydrated iron oxide on the surface of zinc oxide particles, by way of example, an aqueous solution of a water-soluble iron salt is added to an aqueous suspension of zinc oxide particles in an amount of 0.1–20% by weight in terms of iron relative to the zinc oxide, and a neutralization agent is then added to the mixture to neutralize the suspension. The water-soluble iron salt used includes, for example, ferrous chloride, ferric chloride, ferrous sulfate, ferric sulfate, ferrous nitrate or ferric nitrate, however, it is not limited to those exemplified above. In turn, the neutralization agent used includes, for example, sodium hydroxide, potassium hydroxide or ammonium hydroxide, however, it is not limited to those exemplified above.

After the preparation of aqueous suspension of zinc oxide particles having a layer of hydrated iron oxide on the surface, aqueous solutions of a water-soluble silicate and a water-soluble zinc salt are added to the thus prepared aqueous suspension of zinc oxide particles in such a chemically stoichiometric ratio so that they form zinc silicate ($Zn_2SiO_4$) as well as in an amount of 0.5–50% by weight in terms of zinc silicate ($Zn_2SiO_4$) relative to the zinc oxide, the resulting product is washed with water and dried, and the product is then calcined at a temperature of 300–1200° C., preferably at a temperature of 500–1100° C., more preferably at a temperature of 600–1000° C., followed by pulverizing to provide zinc oxide particles which has a cover layer formed of zinc silicate and an average particle diameter of 0.01–0.15 $\mu$m, and in addition, solid solution iron therein.

According to the invention, however, a water-insoluble zinc compound which can be converted to zinc oxide by heating in the air, such as zinc hydroxide, zinc carbonate, basic zinc carbonate, zinc sulfide or zinc oxalate, may be used as a starting raw material for the zinc oxide particle of the invention in place of zinc oxide particles. More specifically, an aqueous solution of a water-soluble iron salt is added to an aqueous suspension of the water-insoluble zinc compound in an amount of 0.1–20% by weight in terms of iron relative to the zinc oxide, and a neutralization agent is then added to the mixture to neutralize the suspension to put it at a pH of 6.0–9.0 thereby to precipitate hydrated iron oxide on the surface of the particles of the water-insoluble zinc compound. Then, an aqueous solution of water-soluble silicate and a water-soluble zinc salt are added to the thus prepared aqueous suspension of water-insoluble zinc compound, and the resulting mixture is washed with water, dried and calcined to form particles of zinc oxide having solid solution iron therein while forming a cover layer formed of zinc silicate on the surface of the particles.

The particle of zinc oxide having solid solution iron therein can be prepared by a further process. A mixture of an aqueous solution of a water-soluble zinc salt and an aqueous solution of a water-soluble iron salt is prepared, and a neutralization agent is added to the mixture to form coprecipitates composed of a water-insoluble zinc compound such as zinc hydroxide, zinc carbonate, basic zinc carbonate, zinc sulfide or zinc oxalate (preferably, zinc hydroxide) and a water-insoluble iron compound (for example, hydrated iron oxide). The coprecipitates are then treated in such a manner as described hereinabove to form particles of zinc oxide having solid solution iron therein while forming a cover layer formed of zinc silicate on the surface of the particles.

The zinc oxide particles having solid solution iron therein as well as a cover layer formed of zinc silicate on the surface have high ability to shield UV-A rays at wavelengths more than 380 nm. Moreover, when the zinc oxide particles are incorporated in a composition such as cosmetics or coating compositions, the surface of the particle is completely masked or separated from the medium used by the cover layer formed of zinc silicate on the surface so that it has remarkably reduced solubility in pure water or chemical reactivity to the components in the compositions, as well as it is substantially completely suppressed in photocatalytic activity.

The invention still further provides a particulate zinc oxide or a zinc oxide particle which has not only a cover layer formed of zinc silicate on the surface in an amount of 0.5–50% by weight, preferably in an amount of 1–15% by weight, in terms of zinc silicate ($Zn_2SiO_4$) relative to the zinc oxide but also cobalt in the form of solid solution in an amount of 0.5–30% by weight, preferably in an amount of 1–25% by weight, more preferably in an amount of 3–20% by weight, in terms of cobalt oxide (CoO).

The zinc oxide particle which contains solid solution cobalt is obtained in the same manner as the solid solution iron containing zinc oxide particle as mentioned above. The solid solution cobalt containing zinc oxide particle is obtained by adding an aqueous solution of a water-soluble cobalt salt to an aqueous suspension of zinc oxide particles in an amount of 0.5–30% by weight in terms of cobalt oxide (CoO) relative to the zinc oxide, adding a neutralization agent to the mixture thereby to form a layer of hydrated cobalt oxide on the surface of the zinc oxide particles, and then, as mentioned hereinbefore, adding aqueous solutions of a water-soluble silicate and a water-soluble zinc salt to the thus prepared aqueous suspension of zinc oxide particles in such a chemically stoichiometric ratio so that they form zinc silicate ($Zn_2SiO_4$) as well as in an amount of 0.5–50% by weight in terms of zinc silicate ($Zn_2SiO_4$) relative to the zinc oxide, washing with water and drying the resulting product, and then calcining the product at a temperature of 300–1200° C., preferably at a temperature of 500–1100° C., more preferably at a temperature of 600–1000° C., thereby diffusing cobalt into the particles to form a solid solution while forming a cover layer formed of zinc silicate on the surface of the particles.

In order to precipitate hydrated cobalt oxide on the surface of zinc oxide particles, by way of example, an aqueous solution of a water-soluble cobalt salt is added to an aqueous suspension of zinc oxide particles in an amount of 0.5–30% by weight in terms of cobalt oxide (CoO) relative to the zinc oxide, and a neutralization agent is then added to the mixture to neutralize the suspension. The water-soluble cobalt salt used includes, for example, cobalt chloride, cobalt sulfate or cobalt nitrate, however, it is not limited to those exemplified above. In turn, the neutralization agent used includes, for example, sodium hydroxide, potassium hydroxide or ammonium hydroxide, however, it is not limited to those exemplified above.

After the preparation of aqueous suspension of zinc oxide particles having a layer of hydrated cobalt oxide on the surface as mentioned above, aqueous solutions of a water-soluble silicate and a water-soluble zinc salt are added to the thus prepared aqueous suspension of zinc oxide particles in such a chemically stoichiometric ratio so that they form zinc silicate ($Zn_2SiO_4$), the resulting product is washed with water and dried, and the product is calcined at a temperature of 300–1200° C., thereby diffusing cobalt into the zinc oxide particles to form solid solution while forming a cover layer formed of zinc silicate.

According to the invention, however, a water-insoluble zinc compound which can be converted to zinc oxide by heating in the air, such as zinc hydroxide, zinc carbonate, basic zinc carbonate, zinc sulfide or zinc oxalate, may be used as a raw material for the zinc oxide particle of the invention in place of zinc oxide particles. More specifically, an aqueous solution of a water-soluble cobalt salt is added to an aqueous suspension of the water-insoluble zinc compound in an amount of 0.5–30% by weight in terms of cobalt oxide (CoO) relative to the zinc oxide, and a neutralization agent is then added to the mixture to neutralize the suspension to put it at a pH of 6.0–9.0 thereby to precipitate hydrated cobalt oxide on the surface of the particles of the water-insoluble zinc compound. Then, an aqueous solution of water-soluble silicate and a water-soluble zinc salt are added to the thus prepared aqueous suspension of water-insoluble zinc compound, and the resulting mixture is washed with water, dried and calcined to form particles of zinc oxide having solid solution cobalt therein while forming a cover layer formed of zinc silicate on the surface of the zinc oxide particles.

The particle of zinc oxide having solid solution cobalt therein can be prepared by a further process. A mixed solution of a water-soluble zinc salt and a water-soluble cobalt salt is neutralized with a neutralization agent to arrange the mixture at a pH of 6.0–9.0 to prepare an aqueous suspension of coprecipitates composed of a water-insoluble zinc compound (for example, zinc hydroxide) and a water-insoluble cobalt compound (for example, hydrated cobalt oxide). Then, as described hereinabove, an aqueous solution of water-soluble silicate and a water-soluble zinc salt are added to the thus prepared aqueous suspension of coprecipitates in such a chemically stoichiometric ratio so that they form zinc silicate ($Zn_2SiO_4$), the resulting product is washed with water and dried, and the product is calcined at a temperature of 300–1200° C., thereby diffusing cobalt into the zinc oxide particles to form solid solution together with the zinc oxide while forming a cover layer formed of zinc silicate on the surface of the zinc oxide particles.

When the amount of the solid solution cobalt in the zinc oxide particle is less than 0.5% by weight in terms of cobalt oxide (CoO), the resulting solid solution cobalt containing zinc oxide particle has substantially no shielding effect of UV rays at a longer wavelength region of 380–420 nm, whereas when the amount of the solid solution cobalt is more than 30% by weight, the resulting solid solution cobalt containing zinc oxide particle has reduced transmission to visible light, that is, they are notably reduced in transparency.

The solid solution cobalt containing zinc oxide particle of the invention is excellent in ability to shield UV rays at a wavelength region as long as 380–420 nm, but also when it is incorporated in a composition such as cosmetics or coating compositions, the particle is completely masked or separated from the medium used by the cover layer formed of zinc silicate on the surface so that it has remarkably reduced solubility in pure water or chemical reactivity to the components in the compositions, as well as it is substantially completely suppressed in photocatalytic activity.

It is preferred that the zinc oxide particle of the invention described above has an average primary particle diameter of not more than 0.15 μm so that it is highly transparent. However, on the other hand, the zinc oxide particle of the invention may have an average primary particle diameter of more than 0.15 μm depending upon its use. The lower limit of average primary particle diameter of the zinc oxide particle of the invention is not specifically limited, but it is usually 0.01 μm.

According to the invention, the zinc oxide particle having solid solution iron or cobalt may have a second coating layer formed of oxide of at least one element selected from the group consisting of aluminum, silicon, tin, zirconium, antimony and rare earth elements on a first cover layer formed of zinc silicate. The amount of the second coating layer is preferably in the range of 0.5–30% by weight, more preferably in the range of 2–15% by weight. The rare earth element used includes, for example, yttrium, lantern, cerium and neodymium.

The zinc oxide particle having the second coating layer is obtained by preparing zinc oxide particles having a cover layer formed of zinc silicate on the surface as mentioned hereinabove, dispersing the thus prepared zinc oxide particles in water to prepare an aqueous suspension, adding an aqueous solution of a water-soluble compound of the element for the second coating layer to the aqueous suspension, adding an acid or an alkali as a neutralization agent to the resulting mixture to neutralize the water-soluble compound thereby precipitating the element on the surface of the zinc oxide particles, followed by separation and, drying if necessary, and calcined.

Water-soluble compounds of aluminum used include, for example, aluminum nitrate, aluminum sulfate or sodium aluminate; water-soluble compounds of silicon used include, for example, sodium silicate; water-soluble compounds of tin used include, for example, tin chloride; water-soluble compounds of zirconium used include, for example, zirconium nitrate; water-soluble compounds of antimony include, for example, antimony chloride; and water-soluble compounds of rare earth elements include, for example, cerium nitrate.

In the preparation of the zinc oxide particle having the second coating layer, an acid or an alkali is used as a neutralization agent as mentioned above, and the acid includes, for example, an inorganic acid such as sulfuric acid or hydrochloric acid, and an organic acid such as acetic acid or oxalic acid, whereas the alkali includes, for example, sodium hydroxide, potassium hydroxide or ammonium hydroxide.

When the second coating layer formed of oxides of two or more of the elements is to be prepared on the first cover layer, such a second coating layer may be formed all at once by using aqueous, solutions of water-soluble compounds of two or more of the elements. However, it is preferred that such a second coating layer be formed one by one by using each of aqueous solutions of water-soluble compounds of two or more of the elements separately. In particular, when the second coating layer contains aluminum oxide, it is preferred that such a coating layer be formed lastly.

According to the invention, after the first cover layer formed of zinc silicate is formed on the surface of starting zinc oxide particles, the second coating layer is formed on the first cover layer, and then the resulting zinc oxide particles may be treated with a surface-treating agent such as organosilicon compounds, polyhydric alcohols or alkanolamines. The surface-treating agent is applied to the zinc oxide particles usually in an amount of 1–20% by weight, preferably in an amount of 1–10% by weight, relative to the zinc oxide.

The organosilicon compound used includes, for example, organopolysiloxanes such as methyl hydrogen polysiloxane or dimethyl polysiloxane, and silane coupling agents such as triethoxyvinylsilane or diphenyldimethoxysilane. The polyhydric alcohol used includes, for example, trimethylol ethane, trimethylolpropane or pentaerythritol while the alkanolamine used includes, for example, diethanolamine, dipropanolamine, triethanolamine or tripropanolamine. When the amount of the surface-treating agent used is less than 1% by weight relative to the zinc oxide, the zinc oxide particles are not sufficiently improved in dispersibility whereas when the amount of the surface-treating agent used is more than 20% by weight relative to the zinc oxide, the improvement in dispersibility is saturated and economically disadvantageous.

As a further treatment, after the formation of the first cover layer on the surface of zinc oxide particles and/or the second coating layer thereon, the zinc oxide particles may be further surface-treated with a higher fatty acid of 10–30 carbon atoms such as lauric acid, stearic acid or palmitic acid, an alkyl ester of such a higher fatty acid such as octyl palmitate, a metal salt or a metal soap of such a higher fatty acid such as aluminum stearate or aluminum laurate. The metal species in the metal soap is not limited to aluminum, and it may be, for example, lithium, magnesium, calcium, strontium, barium, zinc or tin.

As mentioned above, when a further surface-treated layer is formed on the zinc oxide particles by using a surface-treating agent such as a higher fatty acid, a higher fatty acid ester or metal soap, the amount of surface-treating agent used is usually in the range of 1–20% by weight, preferably in the range of 1–10% by weight, relative to the zinc oxide.

When the amount of surface-treating agent used is less than 1% by weight relative to the zinc oxide, the zinc oxide particles are not sufficiently improved in dispersibility whereas when the amount of the surface-treating agent used is more than 20% by weight relative to the zinc oxide, the improvement in dispersibility is saturated and economically disadvantageous.

The zinc oxide particles which are surface-treated with a surface-treating agent as above mentioned is obtained by mixing a predetermined amount of surface-treating agent with zinc oxide particles having the first cover layer (and the second coating layer) thereon and then pulverizing the resulting mixture. The surface-treated zinc oxide particles are obtained also by pulverizing zinc oxide particles having the first cover layer (and the second coating layer) thereon and then mixing with the zinc oxide particles with a surface-treating agent. As a further method, the zinc oxide particles having the first cover layer (and the second coating layer) thereon are dispersed in an appropriate medium, for example, water, an alcohol or an ether, and a surface-treating agent is added to the resulting suspension. After the mixture is stirred, the resulting product is separated, dried and pulverized to provide the desired surface-treated zinc oxide particles. Alternatively, the mixture may be evaporated to dryness, followed by pulverization to provide the desired surface-treated zinc oxide particles.

As set forth above, the zinc oxide particle of the invention has a cover layer formed of zinc silicate on the surface. Accordingly, if it is incorporated in a thermoplastic resin such as polyethylene terephthalate or polycarbonate, it does not promote the decomposition of the resin, in contrast to the known zinc oxide particles. The zinc oxide particle of the invention can be also suitably incorporated in other resin products. Furthermore, the zinc oxide particle of the invention has very small solubility in pure water or diluted sulfuric acid as well as much reduced photocatalytic activity, and hence it can be used in various coating compositions inclusive ones for outdoor use which must be resistant to acid rain.

The zinc oxide particle of the invention may be incorporated in resin compositions or coating compositions in an amount of 1–80% by weight.

When zinc oxide is to be used in cosmetics, the generation of reactive oxygen species by photocatalytic activity that zinc oxide possesses must be restrained in order to protect the human body. It is also known that reactive oxygen species are generated by the action of UV rays. The reactive oxygen species include superoxide, hydrogen peroxide, hydroxyl radical and singlet oxygen among others, and they attack lipid, saccharide, protein or DNA to bring about lipid peroxidation, protein denaturation, DNA lesion or enzyme inhibition, and as results, it is said that various kinds of illness such as skin carcinoma or photoinduced senescence of the human skin are caused or accelerated.

Accordingly, it is important not only to restrain the generation of reactive oxygen species induced by UV rays but also to suppress the photocatalytic activity that zinc oxide inherently possesses in order to protect the human body from the above-mentioned skin lesion.

The zinc oxide particle of the invention contains solid solution iron or cobalt therein so that it is able to shield UV-A rays at long wavelengths of around 400 nm as well as the inherent shielding ability of UV rays. Consequently, the zinc oxide particle of the invention is able to protect the human body from the reactive oxygen species generated by UV rays, but also it is especially suitable for use in sunscreen cosmetics because it has on the surface a cover layer formed of inactive zinc silicate crystals which separates the particle completely from the surrounding substances so that it restrains effectively the generation of reactive oxygen species induced by photocatalytic activity that zinc oxide inherently possesses.

In the preparation of cosmetics, the zinc oxide particle of the invention is incorporated therein in an amount of 1–80% by weight.

EXAMPLES

The invention is now described with reference to examples, however, the invention is not limited thereto. In the following examples and comparative examples, ultrafine zinc oxide particles (FINEX-25 available from Sakai Chemical Industry Co., Ltd.) having an average primary particle diameter of 0.06 μm produced by evaporating and oxidizing electrolytic zinc metal were used as raw materials for the production of ultrafine zinc oxide particles of the invention, unless specifically indicated.

Example 1

An aqueous solution of sodium silicate (1.3% by weight in terms of $SiO_2$ relative to the zinc oxide undermentioned) and an aqueous solution of zinc sulfate (3.7% by weight in terms of ZnO relative to the zinc oxide undermentioned) were added to an aqueous suspension of ultrafine zinc oxide particles (having a zinc oxide concentration of 100 g/L) at a temperature of 60° C. with stirring.

The suspension was then arranged at a pH of 7.5 by using an aqueous solution of sodium hydroxide and aged for 30 minutes. The suspension was cooled to room temperature, filtered, washed with water, and the resulting product was heated and dried at a temperature of 120° C. for 5 hours.

The product was then calcined at a temperature of 800° C. for 60 minutes, pulverized with a jet mill, thereby providing zinc oxide particles having on the surface a cover layer formed of zinc silicate in an amount of 5% by weight in terms of zinc silicate ($Zn_2SiO_4$) relative to the zinc oxide.

Example 2

An aqueous solution of sodium silicate (4.0% by weight in terms of $SiO_2$ relative to the zinc oxide undermentioned) and an aqueous solution of zinc sulfate (11.0% by weight in terms of ZnO relative to the zinc oxide undermentioned) to an aqueous suspension of ultrafine zinc oxide particles (having a zinc oxide concentration of 100 g/L), and otherwise in the same manner as in Example 1, zinc oxide particles having on the surface a cover layer formed of zinc silicate in an amount of 15% by weight in terms of zinc silicate ($Zn_2SiO_4$) relative to the zinc oxide were obtained.

Example 3

An aqueous solution of sodium silicate (1.3% by weight in terms of $SiO_2$ relative to the zinc oxide undermentioned) and an aqueous solution of zinc sulfate (3.7% by weight in terms of ZnO relative to the zinc oxide undermentioned) were added to an aqueous suspension of basic zinc carbonate (having a concentration of 100 g/L in terms of zinc oxide) at a temperature of 60° C. with stirring.

The suspension was then arranged at a pH of 7.5 by using an aqueous solution of sodium hydroxide and aged for 30 minutes. The suspension was cooled to room temperature, filtered, washed with water, and the resulting product was heated and dried at a temperature of 120° C. for 5 hours.

The product was then calcined at a temperature of 800° C. for 60 minutes to form zinc oxide particles and the particles were pulverized with a jet mill, thereby providing zinc oxide particles having on the surface a cover layer formed of zinc silicate in an amount of 5% by weight in terms of zinc silicate ($Zn_2SiO_4$) relative to the zinc oxide.

Example 4

An aqueous solution of sodium silicate (1.3% by weight in terms of $SiO_2$ relative to the zinc oxide undermentioned) and an aqueous solution of zinc sulfate (3.7% by weight in terms of ZnO relative to the zinc oxide undermentioned) were added to an aqueous suspension of ultrafine zinc oxide particles (having a zinc oxide concentration of 100 g/L) at a temperature of 60° C. with stirring.

The suspension was then arranged at a pH of 7.5 by using an aqueous solution of sodium hydroxide and aged for 30 minutes. The suspension was cooled to room temperature, filtered, washed with water, and the resulting product was heated and dried at a temperature of 120° C. for 5 hours.

The product was then calcined at a temperature of 800° C. for 60 minutes in the air and pulverized with a hammer mill. The product was dispersed in water so that it had a zinc oxide concentration of 100 g/L and ground with a sand mill thereby to provide an aqueous dispersion of ultrafine zinc oxide particles.

The aqueous suspension of ultrafine zinc oxide particles was heated to a temperature of 60° C. with effective stirring, and then an aqueous solution of sodium aluminate was added to the suspension in an amount of 3% by weight in terms of $Al_2O_3$ relative to the zinc oxide and the suspension was aged for 10 minutes. After the suspension was neutralized to a pH of 7.0 by using an aqueous solution of sulfuric acid and aged for 30 minutes, the suspension was filtered, washed with water and heated and dried at a temperature of 120° C. for 5 hours.

The resulting product was pulverized with a jet mill to provide ultrafine zinc oxide particles having on the surface a first cover layer formed of zinc silicate in an amount of 5% by weight in terms of zinc silicate ($Zn_2SiO_4$) relative to the zinc oxide and a second coating layer formed of hydrated aluminum oxide in an amount of 3% by weight in terms of $Al_2O_3$ on the surface of the first cover layer.

Example 5

Methyl hydrogen polysiloxane (Silicone Oil KF-99 available from Shin-etsu Kagaku K. R.) was sprayed on the ultrafine zinc oxide particles obtained in Example 1 with stirring with a homogenizer in an amount of 3% by weight relative to the zinc oxide to provide ultrafine zinc oxide particles which were surface-treated with methyl hydrogen polysiloxane.

Comparative Example 1

An aqueous solution of sodium silicate was added to an aqueous suspension of ultrafine zinc oxide particles (having a zinc oxide concentration of 100 g/L) at a temperature of 60° C. with stirring in an amount of 5.0% by weight in terms of $SiO_2$ relative to the zinc oxide. The suspension was arranged at a pH of 7.5 by using an aqueous solution of sulfuric acid and aged for 30 minutes. The suspension was cooled to room temperature, filtered, washed with water, and heated and dried at a temperature of 120° C. for 5 hours in the air. The product was pulverized with a jet mill to provide ultrafine zinc oxide particles having on the surface a coating formed of hydrated silicon oxide in an amount of 5% by weight in terms of $SiO_2$.

Comparative Example 2

Ultrafine zinc oxide particles FINEX-25 available from Sakai Chemical Industry Co., Ltd. were selected as zinc oxide particles of this comparative example.

Various kinds of performance tests were carried out in order to examine their structures and characteristics with respect to the ultrafine zinc oxide particles of Examples 1–5 and Comparative Examples 1 and 2.

Performance Test 1

(Identification of cover layer formed of zinc silicate by X-ray diffractiometry)

Figure 2:
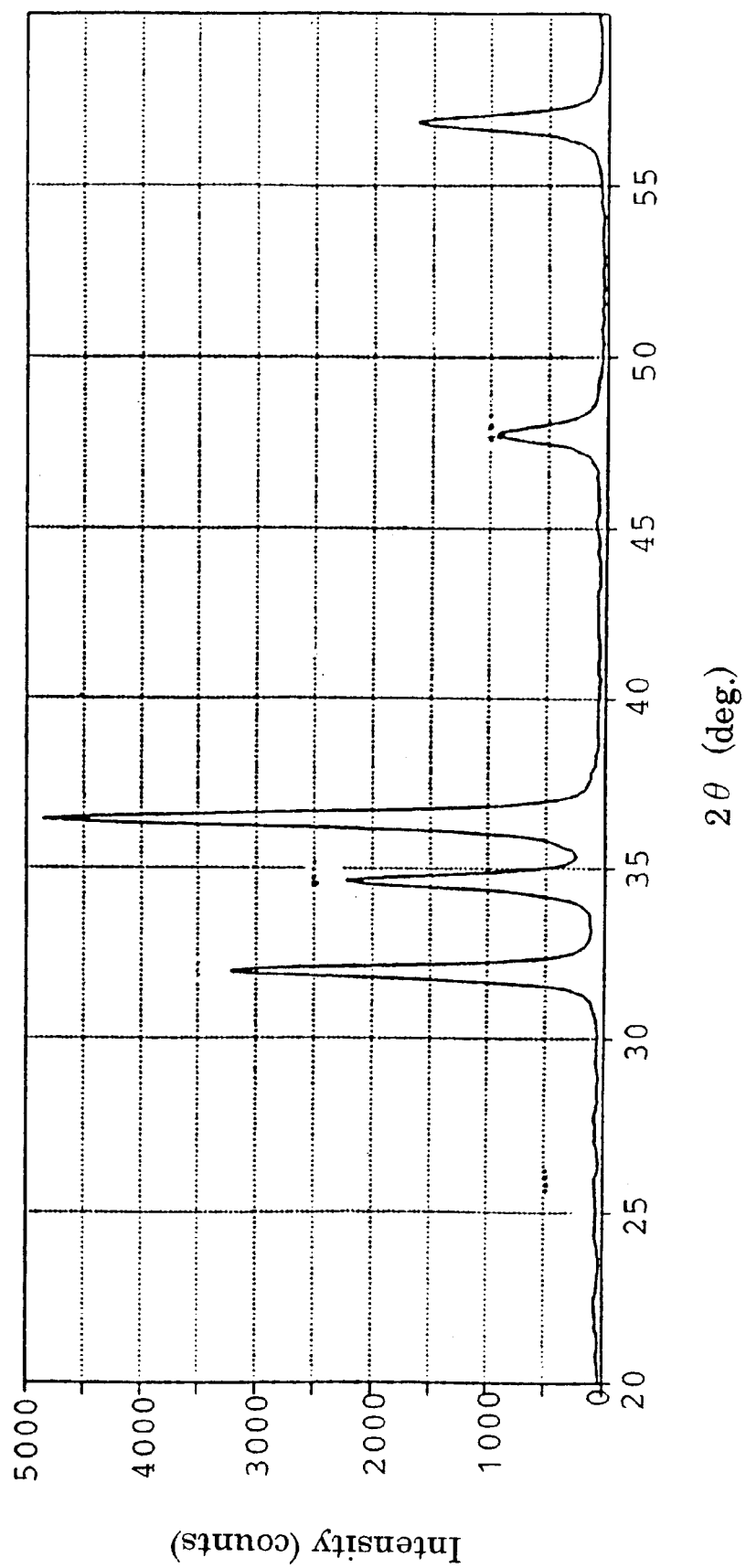
FIG. 2 is an X-ray diffraction chart of ultrafine zinc oxide particles as comparison (Comparative Example 2)

FIG. 1 shows an X-ray diffraction chart of ultrafine zinc oxide particles obtained in Example 1 with a measuring range of 2θ of 20° to 60°. For comparison, FIG. 2 shows an X-ray diffraction chart of ultrafine zinc oxide particles of Comparative Example 2.

The ultrafine zinc oxide particles obtained in Example 1 were found to have diffraction peaks of $\beta$-$Zn_2SiO_4$ at a 2θ of around 22° and 26°. The ultrafine zinc oxide particles obtained in Example 3 were also found to show the same X-ray diffraction patterns.

Performance Test 2

The solubility of zinc oxide from the ultrafine zinc oxide particles obtained in Examples 1 to 4 and Comparative Examples 1 and 2 in pure water or an aqueous solution of sulfuric acid of pH 4 (i.e., 0.0005% by weight concentration) was measured by an atomic absorptiometric method. The results are shown in Table 1. The test was not carried out with the ultrafine zinc oxide particles obtained in Example 5 since they were water-repellent. As seen in Table 1, the ultrafine zinc oxide particles of the invention were found to have very small solubility in pure water or in an aqueous solution of sulfuric acid.

TABLE 1

| | Solubility at 25° C. (ppm) | |
|---|---|---|
| | Pure Water | Aqueous Solution of $H_2SO_4$ |
| Example 1 | 1 | 3.8 |
| 2 | 1 | 4.1 |
| 3 | 1 | 3.0 |
| 4 | 1 | 2.6 |
| Comparative Example 1 | 1 | 10 |
| 2 | 4.1 | 111 |

Performance Test 3

The chemical reactivity of the ultrafine zinc oxide particles obtained in Examples 1 to 3 and Comparative Examples 1 and 2 to fatty acids was examined. Three grams of ultrafine zinc oxide particles were mixed with 27 g of oleic acid (special chemical grade available from Kanto Kagaku K.K.) at room temperature to prepare a suspension. The suspension was put in a warm air chamber maintained at a temperature of 120° C. so that zinc oxide was allowed to react with oleic acid (having a melting point of 24° C.) to form zinc oleate (having a melting point of 78° C.) and the suspension was observed whether the reaction in fact took place at a temperature of 120° C.

The ultrafine zinc oxide particles obtained in both Comparative Examples 1 and 2 were found to react with oleic acid under the above conditions to form zinc oleate with the results that the suspension was found to become a transparent solution. In contrast, none of the ultrafine zinc oxide particles obtained in Examples 1 to 3 were found to react with oleic acid under the above conditions so that the suspension remained the same. Accordingly, it is understood that the ultrafine zinc oxide particles of the invention have effectively restrained reactivity to fatty acids.

Performance Test 4

The chemical reactivity of the ultrafine zinc oxide particles obtained in Examples 1 to 4 and Comparative Examples 1 and 2 to a water-soluble acrylic polymer having carboxylic groups therein (acrylic acid-alkyl acrylate copolymer, Carbopol 934, available from Goodrich) was examined.

The polymer was dissolved in water to prepare an aqueous solution and the solution was arranged at a pH of 6.5 with an aqueous solution of potassium hydroxide to prepare an aqueous gel containing 0.2% by weight of the water-soluble polymer. The ultrafine zinc oxide particles were added to the aqueous gel so that the resulting mixture had a concentration of 12% by weight of the ultrafine zinc oxide particles and the mixture was stirred for 5 minutes with a homogenizer at a rate of 5000 rpm. The thus prepared slurry was placed in a thermostatic oven maintained at a temperature of 38° C. and after leaving standing for 7 days, the viscosity of the slurry was measured at room temperature (25° C.) with a B type viscometer. The results are shown in Table 2. No test was carried out on the ultrafine zinc oxide particles obtained in Example 5 since they were water-repellent.

TABLE 2

| | Viscosity of Slurry at 25° C. (cps) | |
|---|---|---|
| | Initial | After Seven Days |
| Example 1 | 30500 | 22300 |
| 2 | 31000 | 22800 |
| 3 | 32000 | 23500 |
| 4 | 33000 | 25100 |
| Comparative Example 1 | 12000 | 2300 |
| 2 | 9200 | 2700 |

As clearly seen in Table 2, since the ultrafine zinc oxide particles of the invention had almost no reactivity to the polymer, the aqueous gel of the polymer retained the gel structure and hence high viscosity after many hours. In contrast, the ultrafine zinc oxide particles of Comparative Example 1 and the ultrafine zinc oxide particles of Comparative Example 2 which had no cover layer on the surface were found to react with the carboxyl groups of the polymer, and possibly because of induced change of the gel structure, the viscosity was found to remarkably reduced as time passes.

Performance Test 5

The compounding performance of the ultrafine zinc oxide particles obtained in Examples 1 to 3 and Comparative Examples 1 and 2 with resins was examined.

Three grams of ultrafine zinc oxide particles and 7 g of polyethylene terephthalate resin powder (TR-4550BH available from Teijin K.K.) were mixed together and dried at a temperature of 120° C. for 15 hours to prepare a sample resin compounding. The sample was extruded with a piston under a load of 875 g from a melt indexer (Model C5059D available from Toyo Seiki K.K.) at a temperature of 260° C. Based on the time required for extrusion and the amount extruded, the amount extruded in ten minutes was measured as an index for fluidity of the sample. The results are shown in Table 3.

TABLE 3

|  | Melt Flow Rates (g/10 min.) |
| --- | --- |
| Example 1 | 132 |
| 2 | 140 |
| 3 | 134 |
| Comparative Example 1 | 1340 |
| 2 | 440 |
| Resin only | 154 |

As clearly seen in Table 3, the ultrafine zinc oxide particles of Comparative Example 1 had a coating formed of hydrated silicon oxide and the crystal water of the silicon oxide was found to decompose the polyethylene terephthalate resin at the temperature of 260° C., and as results, a liquid material of a very small viscosity was formed. The super-fine zinc oxide particles of Comparative Example 2 was also found to increase the melt flow rate of the compounding compared with the melt flow rate of the resin only so that they have a tendency to decompose the polyethylene terephthalate resin.

In contrast, the ultrafine zinc oxide particles of the invention had a cover layer formed of zinc silicate containing no crystal water on the surface so that they caused no decomposition of polyethylene terephthalate resin at the temperature of 260° C. Therefore, the ultrafine zinc oxide particles of the invention can be suitably incorporated in a polyethylene terephthalate resin for the production of sunscreen agents without a problem of hydrolysis of the resin.

Performance Test 6

The UV ray shielding ability and visible transparency of the ultrafine zinc oxide particles obtained in Examples 1 to 5 and Comparative Examples 1 and 2 were examined.

One and a half grams of ultrafine zinc oxide particles were added to 7.9 g of squalane (available from Nikko Chemicals K.K.) and 0.6 g of surfactant (Span 80 available from Kao Corporation) and the mixture was conditioned with a paint shaker (Model 5410 available from Red Devil) to prepare a coating composition. The composition was coated on a polyethylene terephthalate film with a bar coater No. 6 to prepare a sample.

Using a visible/ultraviolet spectrophotometer (Model V-550 available from Nippon Bunko K.K.), the shielding ability of UV-A at wavelengths of 350 nm and the transmittance to visible rays at wavelengths of 550 nm of the film-were measured. The results are shown in Table 4.

TABLE 4

|  | Transmittance of Rays (%) | |
| --- | --- | --- |
|  | 350 nm | 550 nm |
| Example 1 | 13 | 81 |
| 2 | 10 | 85 |
| 3 | 11 | 83 |
| 4 | 12 | 80 |
| 5 | 9 | 84 |
| Comparative Example 1 | 11 | 83 |
| 2 | 13 | 82 |

The ultrafine zinc oxide particles of the invention had a high density cover layer formed of zinc silicate on the surface, but they were found to have high UV ray shielding ability and high transparency to visible rays and they were not at all deteriorated in these properties by the coverage on the surface with zinc silicate.

Example 6

An aqueous solution of ferrous sulfate (4.0% by weight in terms of iron relative to the zinc oxide undermentioned) and an aqueous solution of sodium hydroxide were added simultaneously over a period of 60 minutes to an aqueous suspension of ultrafine zinc oxide particles (having a zinc oxide concentration of 100 g/L) at room temperature with stirring during which the pH of the suspension was maintained at 9. After ageing for 30 minutes, the resulting aqueous suspension was heated to a temperature of 60° C. and then an aqueous solution of sodium silicate (1.3% by weight in terms of $SiO_2$ relative to the zinc oxide) and an aqueous solution of zinc sulfate (3.7% by weight in terms of ZnO relative to the zinc oxide) were added to the suspension.

The suspension was arranged at a pH of 7.5 by using an aqueous solution of sodium hydroxide and aged for 30 minutes. The suspension was cooled to room temperature, filtered, and the solid was washed with water and heated and dried at a temperature of 120° C. for 5 hours in the air.

The dried product was then calcined in the air at a temperature of 900° C. for 60 minutes, pulverized with a jet mill, thereby providing zinc oxide particles having on the surface a cover layer formed of zinc silicate in an amount of 5.0% by weight in terms of zinc silicate ($Zn_2SiO_4$) relative to the zinc oxide and containing iron in the form of solid solution in an amount of 4% by weight in terms of iron therein.

Example 7

An aqueous solution of ferrous sulfate (8.0% by weight in terms of iron relative to the zinc oxide undermentioned) was added to an aqueous suspension of ultrafine zinc oxide particles (having a zinc oxide concentration of 100 g/L), and otherwise in the same manner as in Example 6, zinc oxide particles having on the surface a cover layer formed of zi nc silicate in an amount of 5.0% by weight in terms of zinc silicate ($Zn_2SiO_4$) relative to the zinc oxide and containing solid solution iron in an amount of 8% by weight in terms of iron therein.

Example 8

An aqueous solution of ferrous sulfate (4.0% by weight in terms of iron relative to the zinc oxide undermentioned) was added to an aqueous solution of zinc sulfate (having a concentration of 100 g/L in terms of ZnO) and the resulting solution was arranged at a pH of 9 by using an aqueous solution of sodium carbonate. After ageing for 30 minutes, the resulting aqueous suspension was heated to a temperature of 60° C. and then an aqueous solution of sodium silicate (1.3% by weight in terms of $SiO_2$ relative to the zinc oxide) and an aqueous solution of zinc sulfate (3.7% by weight in terms of ZnO relative to the zinc oxide) were added to the suspension.

The suspension was arranged at a pH of 7.5 by using an aqueous solution of sodium hydroxide and aged for 30 minutes. The suspension was cooled to room temperature, filtered, and the solid was washed with water and heated and dried in the air at a temperature of 120° C. for 5 hours.

The product was then calcined in the air at a temperature of 800° C. for 60 minutes, pulverized with a jet mill, thereby forming zinc oxide particles having on the surface a cover layer formed of zinc silicate in an amount of 5.0% by weight in terms of zinc silicate ($Zn_2SiO_4$) relative to the zinc oxide and containing solid solution iron in an amount of 4% by weight in terms of iron therein.

Example 9

The dried product obtained in the same manner as in Example 6 was calcined in the air at a temperature of 800° C. for 60 minutes and pulverized with a hammer mill. The product was dispersed in water so that the resulting suspension had a zinc oxide concentration of 100 g/L and ground with a sand mill, thereby to provide an aqueous suspension of ultrafine zinc oxide particles.

The aqueous suspension of ultrafine zinc oxide particles was heated to a temperature of 60° C. with stirring, and then an aqueous solution of sodium aluminate was added to the suspension in an amount of 3% by weight in terms of $Al_2O_3$ relative to the zinc oxide and the suspension was aged for 10 minutes, followed by neutralization with an aqueous solution of sulfuric acid to a pH of 7.0.

After ageing for 30 minutes, the suspension was filtered, washed with water and heated and dried at a temperature of 120° C. for 5 hours.

The resulting product was pulverized with a jet mill to provide ultrafine zinc oxide particles having on the surface a first cover layer formed of zinc silicate in an amount of 5% by weight in terms of zinc silicate ($Zn_2SiO_4$) relative to the zinc oxide and a second coating layer formed of hydrated aluminum oxide in an amount of 3% by weight in terms of $Al_2O_3$ on the surface of the first cover layer, and in addition, containing iron therein in the form of solid solution in an amount of 8% by weight in terms of iron relative to the zinc oxide.

Comparative Example 3

A mixture of 92 parts by weight of ultrafine zinc oxide particles FINEX-25 and 8 parts by weight of ultrafine iron oxide particles (FRO-3 available from Sakai Chemical Industry Co., Ltd.) was prepared.

Comparative Example 4

Ultrafine zinc oxide particles FINEX-25 available from Sakai Chemical Industry Co., Ltd. were selected as zinc oxide particles of this comparative example.

Various kinds of performance tests were carried out in order to examine the structures and characteristics with respect to the ultrafine zinc oxide particles obtained in Examples 6 to 9 and Comparative Examples 3 and 4.
Performance Test 7
(Identification of layer formed of zinc silicate by X-ray diffractiometry)

The ultrafine zinc oxide particles obtained in Examples 6 and 8 were found to show substantially the same X-ray diffraction patterns as those of the ultrafine zinc oxide particles obtained in Example 1, having diffraction peaks of $\beta$-$Zn_2SiO_4$ at a $2\theta$ of around 22° and 26°.
Performance Test 8

In the same manner as in Performance Test 3, the ultrafine zinc oxide particles obtained in Examples 6 and 7 were mixed with oleic acid at room temperature, respectively, to prepare suspensions. The suspensions were maintained at a temperature of 120° C., however, they were found not to react with oleic acid and to remain the same as they initially were.
Performance Test 9

The UV ray shielding ability and visible transparency of the ultrafine zinc oxide particles obtained in Examples 6 to 9 and Comparative Examples 3 and 4 were examined.

Two grams of ultrafine zinc oxide particles containing solid solution iron therein, 4 g of a cold setting acrylic resin (A-132 having a non-volatile content of 50% by weight available from Dainippon Ink Kagaku Kogyo K.K.) and a solvent were conditioned with a paint shaker (Model 5410 available from Red Devil) to prepare a dispersion of the ultrafine zinc oxide particles. A further amount of 12 g of the same cold setting acrylic resin as the above was added to the dispersion, and the dispersion was stirred to prepare a stable dispersion useful as a coating composition containing 20% by weight of ultrafine zinc oxide particles which contained solid solution iron therein. The composition was coated on a polyethylene terephthalate film with a bar coater No. 10 and dried to prepare a sample.

Using a visible/ultraviolet spectrophotometer (Model V-550 available from Nippon Bunko K.K.), the shielding ability of UV-A rays at wavelengths of 350 nm and 385 nm and the transmittance to visible right at a wavelengths of 550 nm of the film were measured. The results are shown in Table 5.

TABLE 5

| | Transmittance of Rays (%) | | |
|---|---|---|---|
| | 350 nm | 385 nm | 550 nm |
| Example 6 | 5 | 31 | 76 |
| 7 | 2 | 28 | 75 |
| 8 | 4 | 30 | 77 |
| 9 | 4 | 33 | 79 |
| Comparative Example 3 | 3 | 46 | 55 |
| 4 | 4 | 50 | 80 |

As clearly seen in Table 5, the ultrafine zinc oxide particles of the invention were found to have a small transmittance to UV-A rays and to be improved in the shielding ability of UV rays at longer wavelengths than 380 nm at which the absorption of UV rays of the known zinc oxide ceases. Besides, the ultrafine zinc oxide particles of the invention were found to have almost the same transparency as the ultrafine zinc oxide particles of Comparative Example 4.
Performance Test 10

The solubility of zinc oxide from the ultrafine zinc oxide particles obtained in Examples 6 to 9 and Comparative Examples 3 and 4 in pure water or an aqueous solution of sulfuric acid of pH 4 (i.e., 0.0005% by weight concentration) at 25° C. was measured in the same manner as in Performance Test 2. The results are shown in Table 6. As clear from the results in Table 6, the ultrafine zinc oxide particles of the invention were found to have very small solubility in pure water or an aqueous solution of sulfuric acid.

TABLE 6

Solubility at 25° C. (ppm)

|  | Pure Water | Aqueous Solution of $H_2SO_4$ |
| --- | --- | --- |
| Example 6 | less than 1 ppm | 4.0 ppm |
| 7 | less than 1 ppm | 4.4 ppm |
| 8 | less than 1 ppm | 4.5 ppm |
| 9 | less than 1 ppm | 4.0 ppm |
| Comparative Example 3 | 5.1 ppm | 111 ppm |
| 4 | 4.2 ppm | 108 ppm |

Performance Test 11

Outdoor exposure tests were conducted to examine the weather resistance of the ultrafine zinc oxide particles containing solid solution iron therein which were obtained in Examples 6 to 9 and Comparative Examples 3 and 4.

Four grams of ultrafine zinc oxide particles containing solid solution iron therein, 6 g of a cold setting acrylic resin (P-470 having a solid content of 70% by weight available from Dainippon Ink Kagaku Kogyo K.K.) and a solvent were conditioned with a paint shaker (Model 5410 available from Red Devil) to prepare a dispersion of the ultrafine zinc oxide particles.

A further amount of 45 g of the same cold setting acrylic resin as the above and 0.3 g of a curing agent were added to the dispersion, and the mixture was stirred to prepare a stable dispersion useful as a coating composition containing 10% by weight of ultrafine zinc oxide particles which contained solid solution iron therein.

The composition was coated at a rate of 54 g/cm² on a board of Japanese cedar 23 by 10 by 1.4 centimeters in the longitudinal direction with a paint brush only once. The board was then dried at room temperature for three days and exposed so that it looked toward the south at an angle of 45° from the horizontal for 120 days.

The color differences ΔE of the paint film before and after the exposure were calculated based on the values of L, a and b of the Hunter's color system of the paint film measured using a color-difference meter (Model SM-5 available from Suga Shikenki K.K.). The smaller the value, the better the weather resistance. The results are shown in Table 7.

TABLE 7

|  | Color Difference (ΔE) |
| --- | --- |
| Example 6 | 2.5 |
| 7 | 2.4 |
| 8 | 2.1 |
| 9 | 2.2 |
| Comparative Example 3 | 9.1 |
| 4 | 11.3 |
| Resin only | 6.1 |

As clear from the results in Table 7, the coating composition prepared by using the ultrafine zinc oxide particles of Comparative Examples 3 and 4 were found to provide paint film suffering remarkable discoloration. However, the coating composition prepared by using the ultrafine zinc oxide particles of the invention were found to provide paint film of which discoloration is effectively restrained. That is, the ultrafine zinc oxide particles of the invention are superior in protecting the surface of substrates.

Example 10

An aqueous solution of cobaltous sulfate (12% by weight in terms of cobalt oxide (CoO) relative to the zinc oxide undermentioned) and an aqueous solution of sodium hydroxide were added simultaneously over a period of 60 minutes to an aqueous suspension of ultrafine zinc oxide particles (having a zinc oxide concentration of 100 g/L) at room temperature with stirring during which the pH of the suspension was maintained at 8. After ageing for 30 minutes, the resulting aqueous suspension was heated to a temperature of 60° C. and then an aqueous solution of sodium silicate (2.4% by weight in terms of $SiO_2$ relative to the zinc oxide) and then an aqueous solution of zinc sulfate (6.5% by weight in terms of ZnO relative to zinc oxide) were added to the suspension.

The suspension was arranged at a pH of 7.5 by using an aqueous solution of sodium hydroxide and aged for 30 minutes. The suspension was cooled to room temperature, filtered, and the solid was washed with water and heated and dried in the air at a temperature of 120° C. for 5 hours.

The dried product was then calcined in the air at a temperature of 900° C. for 60 minutes, pulverized with a jet mill, thereby providing zinc oxide particles having on the surface a cover layer formed of zinc silicate in an amount of 8.9% by weight in terms of zinc silicate ($Zn_2SiO_4$) relative to the zinc oxide and containing cobalt in the form of solid solution in an amount of 12% by weight in terms of cobalt oxide (CoO) therein.

Example 11

An aqueous solution of cobaltous sulfate (12% by weight in terms of cobalt oxide (CoO) relative to the zinc oxide undermentioned) was added to an aqueous solution of zinc sulfate (having a concentration of 100 g/L in terms of zinc oxide.

An aqueous solution of sodium carbonate was added to the resulting solution over a period of 60 minutes so that it had a pH of 8, followed by ageing for 30 minutes. The resulting aqueous suspension was heated to a temperature of 60° C. and then an aqueous solution of sodium silicate (2.4% by weight in terms of $SiO_2$ relative to the zinc oxide) and then an, aqueous solution of zinc sulfate (6.5% by weight in terms of ZnO relative to the zinc oxide) were added to the suspension.

The suspension was arranged at a pH of 7.5 by using an aqueous solution of sodium hydroxide and aged for 30 minutes. The suspension was cooled to room temperature, filtered, and the solid was washed with water and heated and dried at a temperature of 120° C. for 5 hours.

The dried product was then calcined in the air at a temperature of 900° C. for 60 minutes, pulverized with a jet mill, thereby providing zinc oxide particles having on the surface a cover layer formed of zinc silicate in an amount of 8.9% by weight in terms of zinc silicate ($Zn_2SiO_4$) relative to the zinc oxide and containing cobalt in the form of solid solution in an amount of 12% by weight in terms of cobalt oxide (CoO) therein.

Example 12

The dried product obtained in the same manner as in Example 11 was calcined in the air at a temperature of 800° C. for 60 minutes and pulverized with a hammer mill. The product was dispersed in water so that the resulting suspension had a zinc oxide concentration of 100 g/L and ground with a sand mill thereby to provide an aqueous suspension of ultrafine zinc oxide particles containing solid solution cobalt therein.

The aqueous suspension of ultrafine zinc oxide particles was heated to a temperature of 60° C. with stirring, and then an aqueous solution of sodium aluminate was added to the suspension in an amount of 3% by weight in terms of $Al_2O_3$ relative to the zinc oxide and the suspension was aged for 100 minutes, followed by neutralization with an aqueous solution of sulfuric acid to a pH of 7.0.

After ageing for 30 minutes, the suspension was filtered, washed with water and heated and dried at a temperature of 120° C. for 5 hours.

The resulting product was pulverized with a jet mill to provide ultrafine zinc oxide particles having on the surface a first cover layer formed of zinc silicate in an amount of 8.9% by weight in terms of zinc silicate ($Zn_2SiO_4$) relative to the zinc oxide and a second coating layer formed of hydrated aluminum oxide in an amount of 3% by weight in terms of $Al_2O_3$ on the surface of the first cover layer, and in addition, containing cobalt therein in the form of solid solution in an amount of 12% by weight in terms of cobalt oxide (CoO) relative to the zinc oxide.

Comparative Example 5

An aqueous solution of cobaltous sulfate (12% by weight in terms of cobalt oxide (CoO) relative to the zinc oxide undermentioned) was added to an aqueous solution of zinc sulfate (having a concentration of 100 g/L in terms of zinc oxide). An aqueous solution of sodium carbonate was added to the resulting solution so that the resulting suspension had a pH of 8, followed by ageing for 30 minutes. The resulting mixture was filtered, and the solid was washed with water and heated and dried at a temperature of 120° C. for 5 hours.

The dried product was then calcined in the air at a temperature of 400° C. for 60 minutes, pulverized with a jet mill, thereby providing zinc oxide particles containing cobalt in the form of solid solution in an amount of 12% by weight in terms of cobalt oxide (CoO) therein.

Comparative Example 6

Ultrafine zinc oxide particles FINEX-25 available from Sakai Chemical Industry Co., Ltd. were selected as zinc oxide particles of this comparative example.

Performance Test 12

(Identification of Cover Layer Formed of Zinc Silicate by X-ray Diffractiometry)

The ultrafine zinc oxide particles obtained in Examples 10 and 11 were found to show substantially the same X-ray diffraction patterns as those of the ultrafine zinc oxide particles obtained in Example 1, having diffraction peaks of $\beta$-$Zn_2SiO_4$ at a 2θ of around 22° and 26°.

Performance Test 13

In the same manner as in Performance Test 3, the ultrafine zinc oxide particles obtained in Examples 10 and 11 were mixed with oleic acid at room temperature, respectively, to prepare suspensions. The suspensions were maintained at a temperature of 120° C., however, they were found not to react with oleic acid and to remain the same as they initially were.

Performance Test 14

The UV ray shielding ability and visible transparency of the ultrafine zinc oxide particles obtained in Examples 10 to 12 and Comparative Examples 5 and 6 were examined.

Two grams of ultrafine zinc oxide particles containing solid solution cobalt therein, 4 g of a cold setting acrylic resin (A-132 having a non-volatile content of 50% by weight available from Dainippon Ink Kagaku Kogyo K.K.) and a solvent were conditioned with a paint shaker (Model 5410 available from Red Devil) to prepare a dispersion of the ultrafine zinc oxide particles containing solid solution cobalt therein. A further amount of 12 g of the same cold setting acrylic resin as the above was added to the dispersion, and the dispersion was stirred to prepare a stable dispersion useful as a coating composition containing 20% by weight of ultrafine zinc oxide particles which contained solid solution cobalt therein. The composition was coated on a polyethylene terephthalate film with a bar coater No. 10 and dried at room temperature for 4 hours to prepare a sample.

Using a visible/ultraviolet spectrophotometer (Model V-550 available from Nippon Bunko K.K.), the shielding ability of A-region ultraviolet rays at wavelengths of 350 nm and 385 nm and the transmittance to visible rays at wavelengths of 550 nm of the film were measured. The results are shown in Table 8 and FIG. 3.

TABLE 8

| | Transmittance of Rays (%) | | |
|---|---|---|---|
| | 350 nm | 385 nm | 550 nm |
| Example 10 | less than 1 | 11 | 73 |
| 11 | less than 1 | 8 | 72 |
| 12 | less than 1 | 10 | 75 |
| Comparative Example 5 | less than 1 | 8 | 64 |
| 6 | less than 1 | 50 | 75 |

Figure 3:
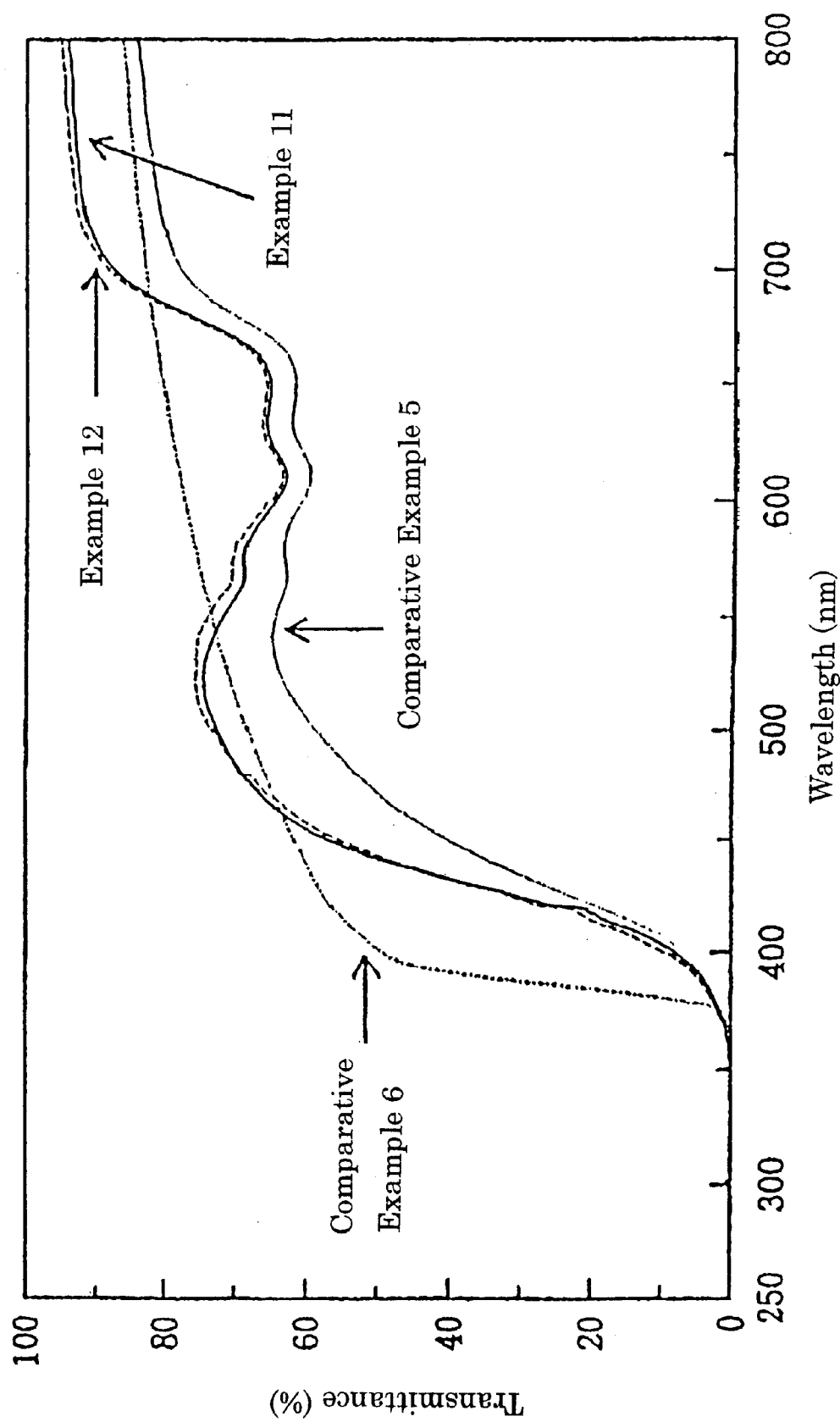
FIG. 3 is a graph showing light transmittance of ultrafine zinc oxide particles containing solid solution cobalt therein according to the invention.

As clearly seen in Table 8 and FIG. 3, the ultrafine zinc oxide particles of the invention were found to have a small transmittance to UV-A rays, in particular, at about 400 nm, and to be improved in the shielding ability of UV rays at longer wavelengths than 380 nm at which the absorption of UV rays of the known zinc oxide ceases. Besides, the ultrafine zinc oxide particles of the invention were found to have almost the same transparency as the ultrafine zinc oxide particles of Comparative Example 6.

Performance Test 15

The solubility of zinc oxide from the ultrafine zinc oxide particles obtained in Examples 10 to 12 and Comparative Examples 5 and 6 in pure water or an aqueous solution of sulfuric acid of pH 4 (i.e., 0.0005% by weight concentration) at 25° C. was measured in the same manner as in Performance Test 2. The results are shown in Table 9. As clear from the results in Table 9, the ultrafine zinc oxide particles of the invention were found to have very small solubility in pure water or an aqueous solution of sulfuric acid.

TABLE 9

| | Solubility at 25° C. (ppm) | |
|---|---|---|
| | Pure Water | Aqueous Solution of $H_2SO_4$ |
| Example 10 | less than 1 ppm | 3.4 ppm |
| 11 | less than 1 ppm | 3.5 ppm |
| 12 | less than 1 ppm | 3.9 ppm |
| Comparative Example 5 | 4.9 ppm | 131 ppm |
| 6 | 4.2 ppm | 108 ppm |

INDUSTRIAL APPLICABILITY OF THE INVENTION

As set forth above, the particulate zinc oxide or ultrafine zinc oxide particles of the invention have on the surface a cover layer formed of zinc silicate and hence they have high UV ray shielding ability and high transparency to visible light while they are suppressed in their photocatalytic activity which they inherently possess. Accordingly, the ultrafine zinc oxide particles of the invention have remarkably reduced solubility in water or in aqueous solution of sulfuric acid and, in addition, because they are suppressed in photocatalytic activity, they are suitable for use as UV ray shielding agents in products in a variety of fields, such as resins, coating compositions or cosmetics.

Furthermore, the ultrafine zinc oxide particles of the invention which have on the surface a cover layer formed of zinc silicate but also which contain solid solution iron or cobalt therein are able to shield UV rays at longer wavelengths than UV-A rays which the known zinc oxide inherently can shield, and yet they are highly transparent.

What is claimed is:

1. A zinc oxide particle having suppressed surface activity, having on the surface a cover layer formed of zinc silicate in an amount of 0.5–50% by weight in terms of zinc silicate ($Zn_2SiO_4$) relative to the zinc oxide.

2. The zinc oxide particle as claimed in claim 1 wherein it is surface-treated with an organosilicon compound, a $C_{10}$ to $C_{30}$ fatty acid, a $C_{10}$ to $C_{30}$ fatty acid ester, a metal soap, a polyhydric alcohol or an alkanolamine in an amount of 1–20% by weight based on the zinc oxide.

3. The zinc oxide particle as claimed in claim 1 wherein it has on the surface a first cover layer formed of zinc silicate and a second coating layer formed of an oxide of at least one element selected from the group consisting of Al, Si, Zr, Sn, Sb and rare earth elements on the first cover layer in an amount of 0.5–30% by weight in terms of oxides relative to the zinc oxide.

4. The zinc oxide particle as claimed in claim 3 wherein it is surface-treated with an organosilicon compound, a $C_{10}$ to $C_{30}$ higher fatty acid, a $C_{10}$ to $C_{30}$ higher fatty acid ester, a metal soap, a polyhydric alcohol or an alkanolamine in an amount of 1–20% by weight based on the zinc oxide.

5. The zinc oxide particle as claimed in claim 1 wherein it has an average particle diameter of not more than 0.15 $\mu$m.

6. The zinc oxide particle as claimed in claim 1 which has a solubility of not more than 2 ppm in terms of zinc in pure water and a solubility of not more than 20 ppm in terms of zinc in an aqueous solution of sulfuric acid having a concentration of 0.0005% by weight.

7. A resin composition which comprises the zinc oxide particle as claimed in claim 1 in an amount of 1–80% by weight.

8. A coating composition which comprises the zinc oxide particle as claimed in claim 1 in an amount of 1–80% by weight.

9. A cosmetic which comprises the zinc oxide particle as claimed in claim 1 in an amount of 1–80% by weight.

10. The zinc oxide particle as claimed in claim 1 wherein it contains cobalt in the form of solid solution in an amount of 0.5–30% by weight in terms of cobalt oxide (CoO) based on the zinc oxide.

11. A process for production of the zinc oxide particle as claimed in claim 1, which comprises:

adding aqueous solutions of a water-soluble silicate and a water-soluble zinc salt to an aqueous suspension of particles of water-insoluble zinc compound in such a chemically stoichiometric ratio so that they form zinc silicate ($Zn_2SiO_4$) and in such an amount of 0.5–50% by weight in terms of zinc silicate ($Zn_2SiO_4$) relative to the zinc oxide to be formed from the water-insoluble zinc compound; and washing the resulting product with water, drying, and heating the product at a temperature of 300–1200° C. thereby forming zinc oxide particles and a cover layer formed of zinc silicate on the surface of the zinc oxide particles.

12. The zinc oxide particle as claimed in claim 1 wherein it contains iron in the form of solid solution in an amount of 0.1–20% by weight based on the zinc oxide.

13. A process for production of the zinc oxide particle as claimed in claim 12, which comprises:

precipitating hydrated iron oxide in an amount of 0.1–20% by weight in terms of iron or hydrated cobalt oxide in an amount of 0.5–30% by weight in terms of cobalt oxide (CoO) on the surface of particles of a water-insoluble zinc compound relative to the zinc oxide to be formed from the water-insoluble zinc compound;

adding aqueous solutions of a water-soluble silicate and a water-soluble zinc salt to an aqueous suspension of the resulting particles of the water-insoluble zinc compound in such a chemically stoichiometric ratio so that they form zinc silicate ($Zn_2SiO_4$) and in such an amount of 0.5–50% by weight in terms of zinc silicate ($Zn_2SiO_4$) relative to the zinc oxide to be formed from the water-insoluble zinc compound; and washing the resulting product with water, drying, and heating the product at a temperature of 300–1200° C. thereby forming zinc oxide particles and a cover layer formed of zinc silicate on the surface of the zinc oxide particles.

14. A process for production of the zinc oxide particle as claimed in claim 12, which comprises:

preparing an aqueous suspension comprising either coprecipitates of zinc and iron or coprecipitates of zinc and cobalt by adding a neutralization agent to either an aqueous solution of a water-soluble zinc salt and a water-soluble iron salt in an amount of 0.1–20% by weight in terms of iron relative to the zinc oxide or an aqueous solution of a water-soluble zinc salt and a water-soluble cobalt salt in an amount of 0.5–30% by weight in terms of cobalt oxide (CoO) relative to the zinc oxide;

adding aqueous solutions of a water-soluble silicate and a water-soluble zinc salt to an aqueous suspension of the resulting particles of the water-insoluble zinc compound in such a chemically stoichiometric ratio so that they form zinc silicate ($Zn_2SiO4$) and in such an amount of 0.5–50% by weight in terms of zinc silicate ($Zn_2SiO_4$) relative to the zinc oxide to be formed from the water-insoluble zinc compound; and the resulting product with water, drying, and heating the product at a temperature of 300–1200° C. thereby forming zinc oxide particles which contains iron or cobalt in the form of solid solution and a cover layer formed of zinc silicate on the surface of the zinc oxide particles.

* * * * *